(12) United States Patent
Hashiguchi et al.

(10) Patent No.: US 9,775,589 B2
(45) Date of Patent: Oct. 3, 2017

(54) RIGID ENDOSCOPE FOR PROSTATE BIOPSY AND TREATMENT INSTRUMENT

(71) Applicant: OLYMPUS CORPORATION, Tokyo (JP)

(72) Inventors: Toshihiko Hashiguchi, Sagamihara (JP); Tadashi Hatano, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/221,984

(22) Filed: Jul. 28, 2016

(65) Prior Publication Data

US 2016/0331359 A1    Nov. 17, 2016

Related U.S. Application Data

(63) Continuation of application No. PCT/JP2014/083950, filed on Dec. 22, 2014.

(30) Foreign Application Priority Data

Jan. 29, 2014  (JP) ................................. 2014-014681

(51) Int. Cl.
*A61B 8/00* (2006.01)
*A61B 10/04* (2006.01)
(Continued)

(52) U.S. Cl.
CPC ................ *A61B 10/04* (2013.01); *A61B 1/00* (2013.01); *A61B 1/00013* (2013.01);
(Continued)

(58) Field of Classification Search
CPC .............. A61B 5/02427; A61B 5/0002; A61B 5/02416; A61B 5/02433; A61B 5/02438;
(Continued)

(56) References Cited

U.S. PATENT DOCUMENTS 6,203,533 B1   3/2001   Ouchi
8,428,710 B2 *  4/2013  Kuriyama .............. A61B 1/018
                                                    604/21
(Continued)

FOREIGN PATENT DOCUMENTS

JP    8-336591 A    12/1996
JP    9-38202 A      2/1997
(Continued)

OTHER PUBLICATIONS

Japanese Office Action dated Sep. 29, 2015 issued in Japanese Patent Application No. 2015-527700.
(Continued)

*Primary Examiner* — Joel Lamprecht

(74) *Attorney, Agent, or Firm* — Scully, Scott, Murphy & Presser, P.C.

(57) ABSTRACT

A rigid endoscope for prostate biopsy includes: an insertion portion including a distal end portion including an ultrasound transmission and reception portion, and a bent portion bent at a predetermined curvature; a treatment instrument insertion channel that passes through inside the bent portion and includes a first opening portion provided on a distal end side and a second opening portion provided on a proximal end side; a shaft-shaped portion installed to extend in a proximal end direction of the bent portion along a straight line passing through an inflection portion provided between the distal end portion and the bent portion; and a grasping portion that includes the shaft-shaped portion.

5 Claims, 18 Drawing Sheets

(51) Int. Cl.
  *A61B 1/00*  (2006.01)
  *A61B 1/303*  (2006.01)
  *A61B 1/307*  (2006.01)
  *A61B 1/31*  (2006.01)
  *A61B 8/12*  (2006.01)
  *A61B 10/02*  (2006.01)
  *A61B 1/018*  (2006.01)
  *A61B 1/05*  (2006.01)
  *A61B 1/07*  (2006.01)
  *A61B 17/00*  (2006.01)

(52) U.S. Cl.
  CPC .......... *A61B 1/00071* (2013.01); *A61B 1/018* (2013.01); *A61B 1/05* (2013.01); *A61B 1/07* (2013.01); *A61B 1/303* (2013.01); *A61B 1/307* (2013.01); *A61B 1/31* (2013.01); *A61B 8/12* (2013.01); *A61B 10/0275* (2013.01); *A61B 2017/00738* (2013.01)

(58) Field of Classification Search
  CPC ..... A61B 5/1123; A61B 5/4812; A61B 5/681; A61B 5/7203
  See application file for complete search history.

(56) References Cited

U.S. PATENT DOCUMENTS

| | | | |
|---|---|---|---|
| 8,608,652 B2* | 12/2013 | Voegele | 600/207 |
| 2011/0060185 A1* | 3/2011 | Ikuma | A61B 5/062 600/104 |
| 2013/0225995 A1* | 8/2013 | Hashiguchi | A61B 1/307 600/439 |
| 2014/0088356 A1* | 3/2014 | Matsuo | A61B 1/0056 600/109 |

FOREIGN PATENT DOCUMENTS

| | | |
|---|---|---|
| JP | 9-84790 A | 3/1997 |
| JP | 10-234653 A | 9/1998 |
| JP | 2001-37775 A | 2/2001 |
| JP | 2002-306497 A | 10/2002 |

OTHER PUBLICATIONS

International Search Report dated Mar. 17, 201 issued in PCT/JP2014/083950.

* cited by examiner

RIGID ENDOSCOPE FOR PROSTATE BIOPSY AND TREATMENT INSTRUMENT

CROSS REFERENCE TO RELATED APPLICATION

This application is a continuation application of PCT/JP2014/083950 filed on Dec. 22, 2014 and claims benefit of Japanese Application No. 2014-014681 filed in Japan on Jan. 29, 2014, the entire contents of which are incorporated herein by this reference.

BACKGROUND OF INVENTION

1. Field of the Invention

The present invention relates to a rigid endoscope for prostate biopsy including a treatment instrument insertion channel and to a treatment instrument that can be inserted into the treatment instrument insertion channel.

2. Description of the Related Art

A procedure of causing a treatment instrument to reach a prostate through a urethra is disclosed in, for example, Japanese Patent Application Laid-Open Publication No. 2001-37775. In this way, the treatment instrument inserted into a human body through the urethra can be used to perform a prostate biopsy for collecting tissue of the prostate to diagnose prostate cancer.

The urethra passes through substantially a center of the prostate, and the treatment instrument needs to be protruded in a direction intersecting with the urethra to collect the tissue of the prostate by the treatment instrument inserted into the urethra. Furthermore, it is preferable to perform the biopsy in a wide range of the prostate to improve accuracy of the diagnosis.

SUMMARY OF THE INVENTION

An aspect of the present invention provides a rigid endoscope for prostate biopsy including: an insertion portion that includes an ultrasound transmission and reception portion that transmits and receives ultrasound, a distal end portion including the ultrasound transmission and reception portion, and a bent portion which is provided on a proximal end side of the distal end portion and which is bent at a predetermined curvature; a treatment instrument insertion channel that passes through inside the bent portion and includes a first opening portion provided on a distal end side and a second opening portion provided on a proximal end side, the treatment instrument insertion channel being installed at a position that allows a treatment instrument protruding from the first opening portion to be housed within an observation range of the ultrasound transmission and reception portion; a shaft-shaped portion that is installed to extend in a proximal end direction of the bent portion along a straight line passing through an inflection portion provided between the distal end portion and the bent portion; and a grasping portion that includes the shaft-shaped portion.

An aspect of the present invention provides a treatment instrument that is at least partially insertable into the treatment instrument insertion channel of the rigid endoscope for prostate biopsy, wherein a part that can be inserted into the treatment instrument insertion channel maintains a shape bent along the treatment instrument insertion channel in a state under no external force.

Further, another aspect of the present invention provides a rigid endoscope for prostate biopsy including: an insertion portion that includes an ultrasound transmission and reception portion that transmits and receives ultrasound, a distal end portion including the ultrasound transmission and reception portion, and a bent portion which is provided on a proximal end side of the distal end portion and which is bent at a predetermined curvature; a treatment instrument insertion channel that passes through inside the bent portion and includes a first opening portion provided on a distal end side and a second opening portion provided on a proximal end side, the treatment instrument insertion channel being installed at a position that allows a treatment instrument protruding from the first opening portion to be housed within an observation range of the ultrasound transmission and reception portion; and a shaft-shaped portion that is installed to extend in a proximal end direction of the bent portion along a straight line coincident with or parallel to a center axis of a connection portion provided between the distal end portion and the bent portion; and a grasping portion that includes the shaft-shaped portion.

Furthermore, yet another aspect of the present invention provides a rigid endoscope for prostate biopsy including: an insertion portion that includes an ultrasound transmission and reception portion that transmits and receives ultrasound, a linear distal end portion including the ultrasound transmission and reception portion, and a bent portion which is provided on a proximal end side of the distal end portion and which is bent at a predetermined curvature; a treatment instrument insertion channel that passes through inside the bent portion and includes a first opening portion provided on a distal end side and a second opening portion provided on a proximal end side, the treatment instrument insertion channel being installed at a position that allows a treatment instrument protruding from the first opening portion to be housed within an observation range of the ultrasound transmission and reception portion; a shaft-shaped portion that is installed to extend in a proximal end direction of the bent portion along a straight line coincident with or parallel to a center axis of the linear distal end portion; and a grasping portion that includes the shaft-shaped portion.

DETAILED DESCRIPTION OF THE PREFERRED EMBODIMENT(S)

Figure 1:
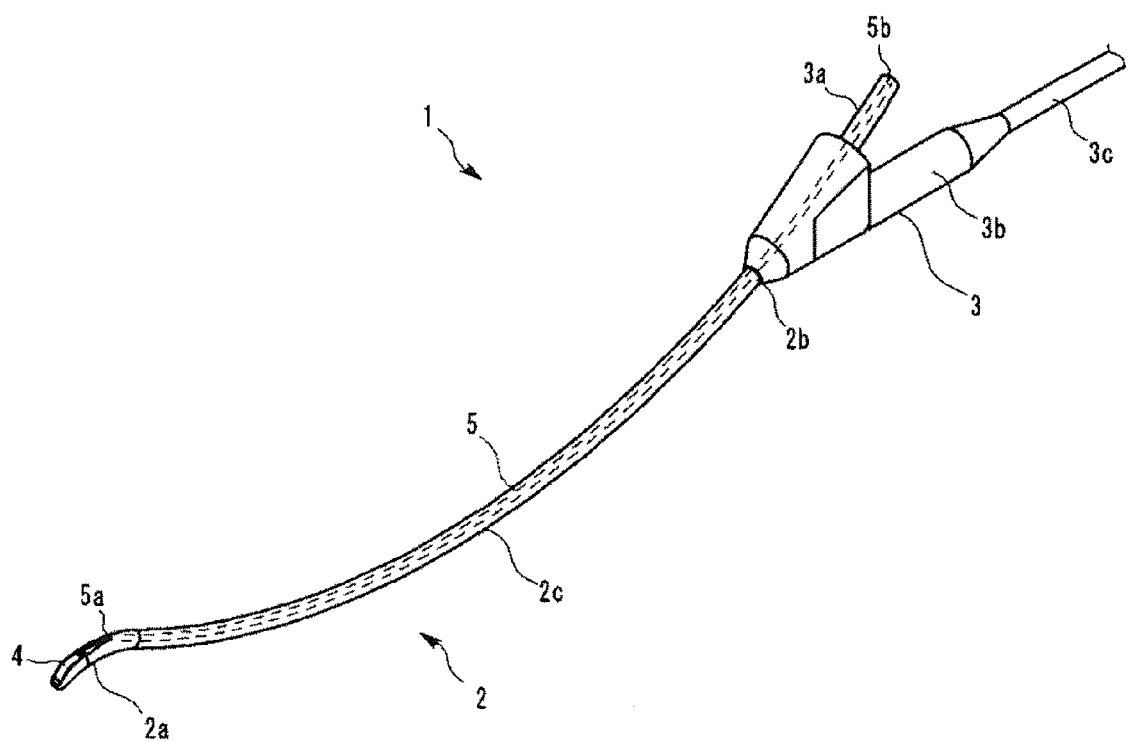
FIG. 1 is a perspective view of a cystourethroscope for prostate biopsy.

Hereinafter, preferred embodiments of the present invention will be described with reference to the drawings. Note that scaling of each constituent element varies in each drawing used in the following description in order to illustrate each constituent element in a size that allows recognizing the constituent element on the drawing, and the present invention is not limited only to the number of the constituent elements, shapes of the constituent elements, ratios of the sizes of the constituent elements, and relative positional relationships between respective constituent elements described in the drawings.

A cystourethroscope for prostate biopsy 1 according to the present invention is a tool inserted into a urethra of a human body and used. Hereinafter, the cystourethroscope for prostate biopsy will be simply called a cystourethroscope. The cystourethroscope 1 is used to perform at least one of observation and treatment of a prostate or a bladder through the urethra.

The cystourethroscope 1 of the present embodiment is, for example, a tool inserted into the urethra and used to perform a prostate biopsy of a human body that is a subject. The cystourethroscope 1 is configured to be able to guide a treatment instrument 20 described later for collecting tissue of the prostate, from outside the body to the prostate through the urethra. The collection of the tissue of the prostate through the urethra will be called a transurethral biopsy.

The cystourethroscope 1 of the present embodiment includes an observation portion 4 that can pick up at least one of an ultrasound tomographic image and an optical image in a state that the cystourethroscope 1 is inserted into the subject and is configured to be able to observe inside the subject, for example. The cystourethroscope 1 of the present embodiment has a form of a so-called rigid endoscope, in which an insertion portion 2 that can be inserted into the urethra is configured to keep a predetermined shape in a natural state under no external force.

Figure 2:
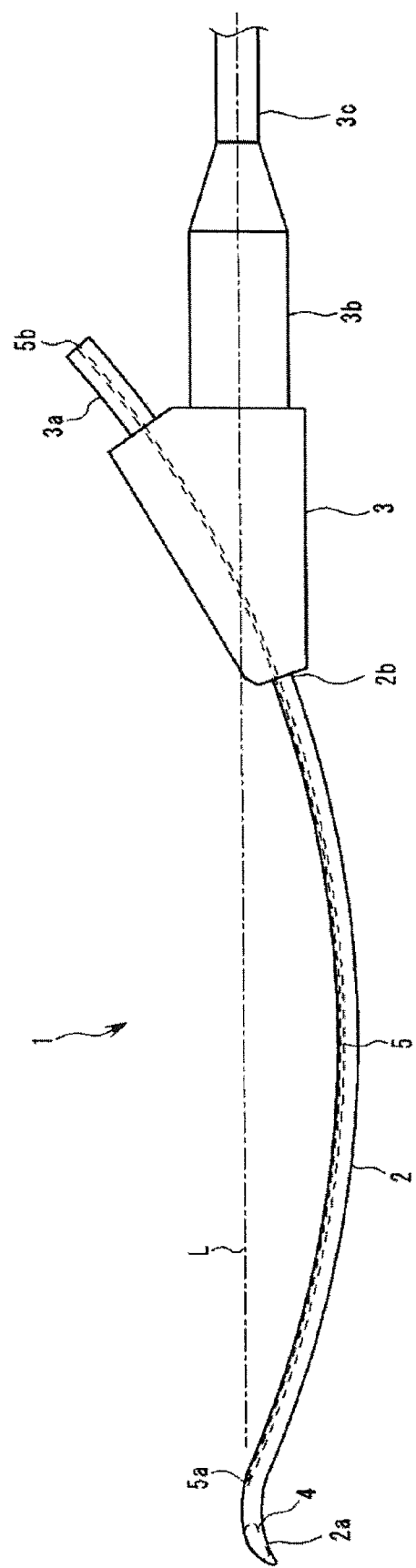
FIG. 2 is a side view of the cystourethroscope for prostate biopsy.

As shown in FIGS. 1 and 2, the cystourethroscope 1 of the present embodiment includes: the elongated insertion portion 2 that can be inserted into the urethra; a grasping portion 3 connected to a proximal end portion 2b of the insertion portion 2; the observation portion 4 installed on a distal end portion 2a of the insertion portion 2; and a treatment instrument insertion channel 5 that allows insertion of the treatment instrument 20.

The insertion portion 2 is an elongated part with a predetermined length and has a cross-sectional shape that allows insertion into the urethra. The cross-sectional shape of the insertion portion 2 can be a shape that allows smooth rotation around a center axis in the urethra and is, for example, a circular shape, an elliptic shape, or an oval shape. The cross-sectional shape and a cross-sectional area of the insertion portion 2 may change in the middle. The observation portion 4 is installed on the distal end portion 2a of the insertion portion 2. A length of the insertion portion 2 is not particularly limited. The insertion portion 2 is provided with a bent portion 2c bent in a predetermined shape. The shape of the insertion portion 2 including the bent portion 2c will be described later.

The grasping portion 3 is a part fixed to the proximal end 2b of the insertion portion 2 and is a part grasped by a user of the cystourethroscope 1 in use. A treatment instrument insertion pipe sleeve 3a in which a second opening portion 5b of the treatment instrument insertion channel 5 described later opens is installed on the grasping portion 3.

The grasping portion 3 is provided with a shaft-shaped portion 3b in a substantially pillar shape extending in a proximal end direction. Although the shaft-shaped portion 3b has a substantially cylindrical shape in the illustrated present embodiment, the shape of the shaft-shaped portion 3b may be a quadrangular prism, an octagonal prism, or the like. The shaft-shaped portion 3b is fixed to the insertion portion 2 and installed. The arrangement of the shaft-shaped portion 3b will be described later.

A cable portion 3c to which an electric cable 6 or the like connected to the observation portion 4 described later is inserted extends from the grasping portion 3. Although not shown, an end portion of the cable portion 3c is provided with a connector portion that can be connected to an ultrasound observation apparatus or a video processor that is an external apparatus not shown. In the present embodiment, the cable portion 3c is installed to extend from an end portion of the shaft-shaped portion 3b along a center axis of the shaft-shaped portion 3b, for example.

The treatment instrument insertion channel 5 is a conduit installed inside the cystourethroscope 1, and both ends open outside the cystourethroscope 1. One end of the treatment instrument insertion channel 5 opens at the distal end portion 2a of the insertion portion 2 or near the distal end portion 2a, and the other end opens at the grasping portion 3.

In other words, the treatment instrument insertion channel 5 is a conduit with an inner diameter that allows insertion of at least part of the treatment instrument 20, and the treatment instrument insertion channel 5 connects a first opening portion 5a provided on the insertion portion 2 of the cystourethroscope 1 and the second opening portion 5b provided on the grasping portion 3. The treatment instrument 20 inserted into the opening portion 5b of the grasping portion 3 passes through the treatment instrument insertion channel 5 and protrudes from the opening portion 5a of the insertion portion 2.

Hereinafter, the shapes of the insertion portion 2 and the treatment instrument insertion channel 5 will be described.

Figure 5:
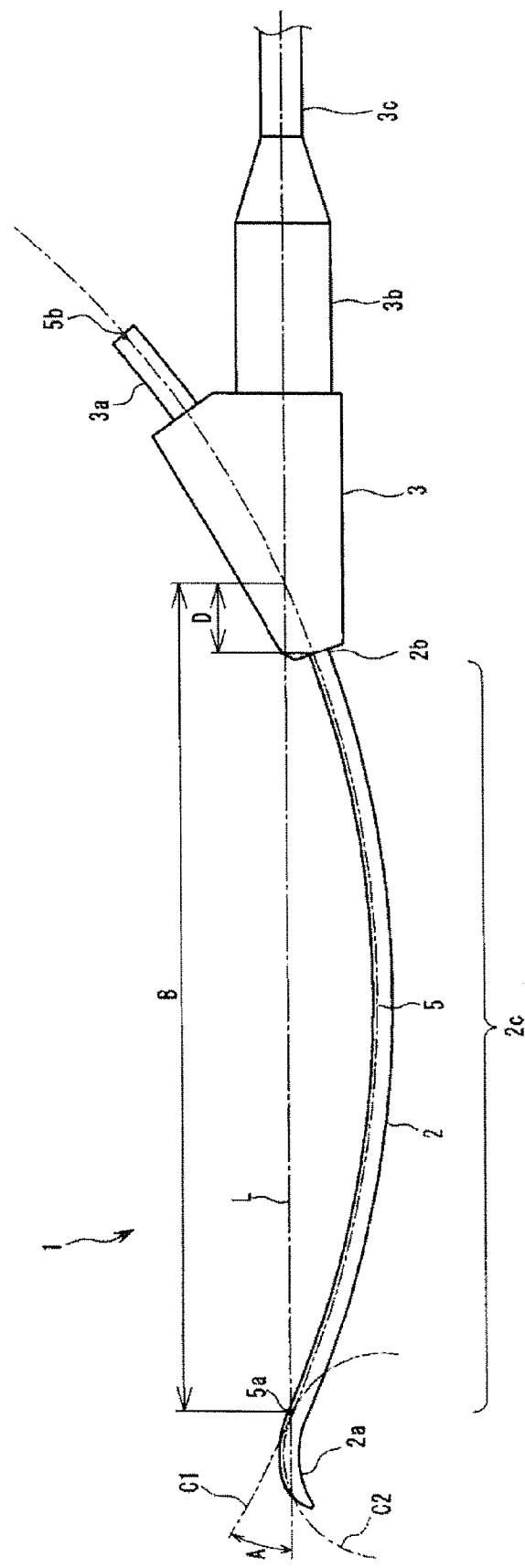
FIG. 5 is a diagram for describing a bending shape of the insertion portion.

As shown in FIG. 5, the insertion portion 2 includes a bent portion 2c configured to maintain a shape bent along a predetermined curve C1 in a state under no external force. The bent portion 2c is provided in a region from the proximal end 2b of the insertion portion 2 to near the first opening portion 5a.

Figure 3:
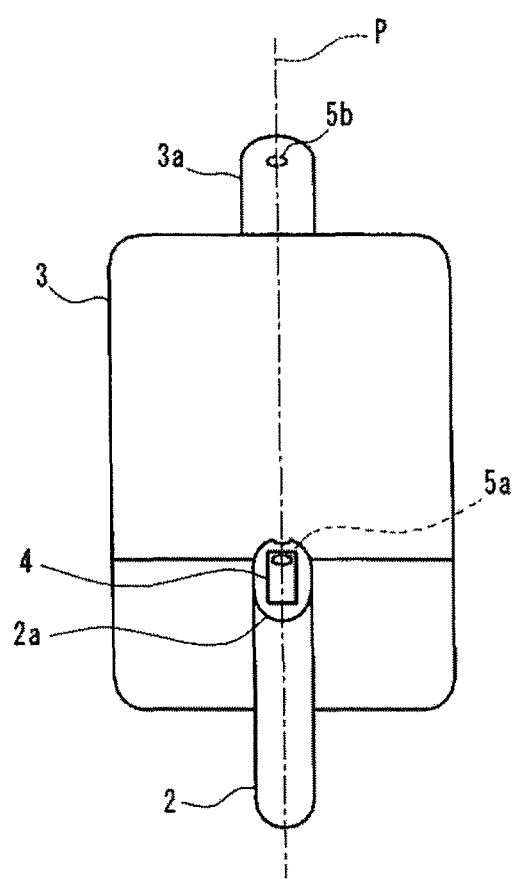
FIG. 3 is a front view of the cystourethroscope for prostate biopsy as viewed from a distal end side of an insertion portion.

The bent portion 2c is bent along the predetermined curve C1 (shown in FIG. 5) passing through the first opening portion 5a and the second opening portion 5b, on a predetermined plane P (shown in FIG. 3) passing through the first opening portion 5a and the second opening portion 5b.

Although a shape of the curve C1 is not particularly limited, an arc with a constant radius of curvature is preferable. Other than the arc, the shape of the curve C1 may be a shape in which the radius of curvature changes, such as an elliptic curve, a hyperbola, and a parabola. In the present embodiment, the curve C1 is, for example, an arc in which the radius of curvature is a substantially constant value of 100 mm or more and 600 mm or less. The radius of curvature of the curve C1 is set such that a protrusion angle A (shown in FIG. 5) relative to a straight line L (described later) of the treatment instrument 20 described later protruding from the first opening portion 5a is 15 degrees to 45 degrees.

The distal end portion 2a of the insertion portion 2 that is a region on a distal end side of the bent portion 2c has a shape bent in an opposite direction of a bending direction of the bent portion 2c or has a straight line shape. When the distal end portion 2a has a bent form, it can be rephrased that the distal end portion 2a is bent in a convex direction of the bending of the bent portion 2c.

Specifically, the distal end portion 2a of the present embodiment is bent along a curve C2 bent in a direction opposite to the bending direction of the curve C1 on the predetermined plane P passing through the first opening portion 5a and the second opening portion 5b. A shape of the curve C2 is not particularly limited. The curve C2 may be an arc with a constant radius of curvature or may have a shape in which the radius of curvature changes, such as an elliptic curve, a hyperbola, and a parabola. In the present embodiment, the curve C2 is an arc with the radius of curvature smaller than that of the curve C1, and a value of the radius of curvature is about 20 mm or more and 40 mm or less.

The insertion portion 2 has a rigidity that maintains the shape described above, in a state under no external force.

As described, the insertion portion 2 has an S-shape with an inflection portion in the middle, the S-shape being bent along the curve C1 that is convex in one predetermined direction and bent along the curve C2 that is convex in the opposite direction of the convex direction of the curve C1, on the predetermined plane P passing through the first opening portion 5a and the second opening portion 5b.

Figure 6:
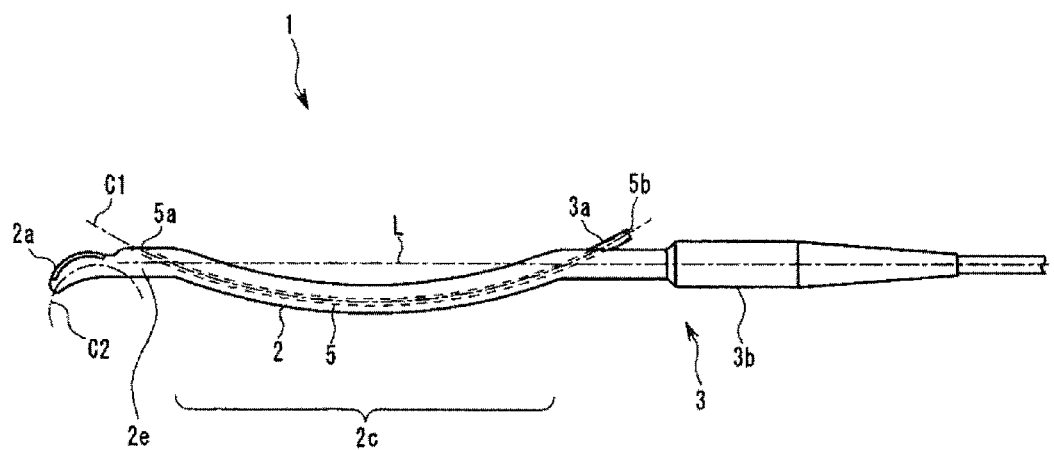
FIG. 6 is a diagram showing a first modification of the cystourethroscope for prostate biopsy.
Figure 7:
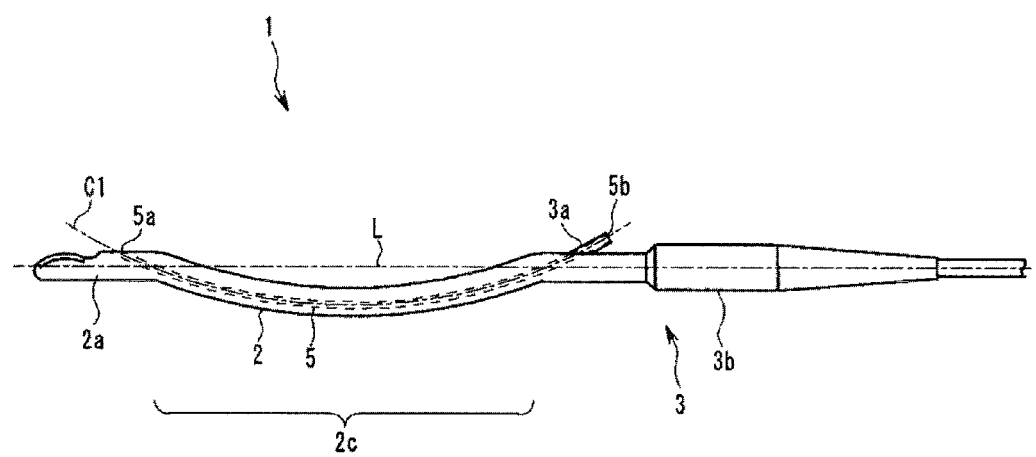
FIG. 7 is a diagram showing a second modification of the cystourethroscope for prostate biopsy.

Note that as shown in a first modification of FIG. 6, a connection portion 2e including a center axis in a straight line shape may be provided between the bent portion 2c and the distal end portion 2a of the insertion portion 2. As shown in a second modification of FIG. 7, the distal end portion 2a of the insertion portion 2 may have a straight line shape. The first and second modifications shown in FIGS. 6 and 7 are the same as the present embodiment shown in FIG. 5 in that the insertion portion 2 includes the inflection portion between the distal end portion 2a and the bent portion 2c.

Figure 4:
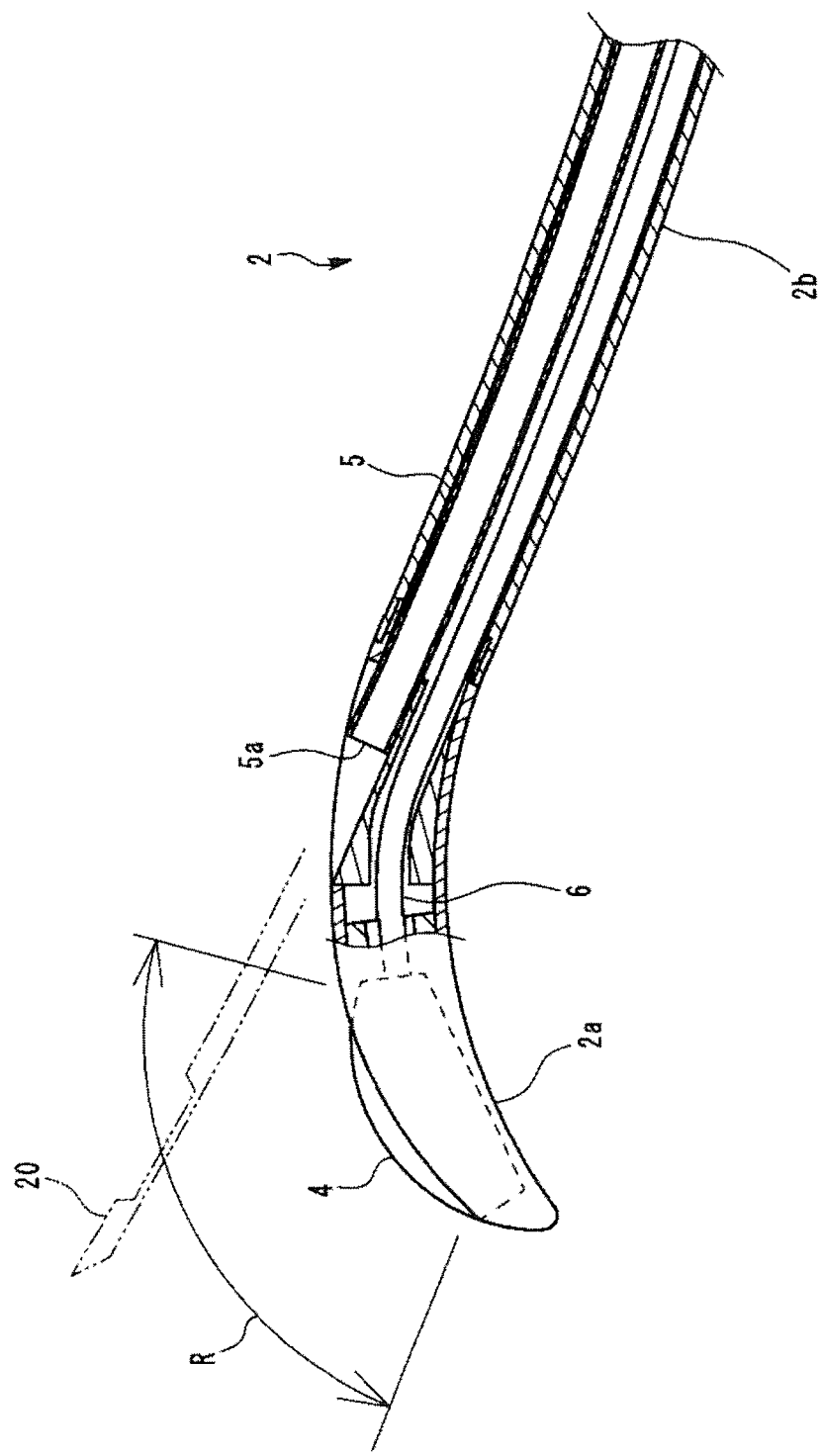
FIG. 4 is a partial cross-sectional view of the insertion portion.

The first opening portion 5a is installed near the distal end of the bent portion 2c or near the proximal end of the distal end portion 2a. In other words, the first opening portion 5a is installed near the inflection portion of the insertion portion 2 in the present embodiment. Therefore, as shown in FIG. 4, the treatment instrument 20 inserted into the treatment instrument insertion channel 5 and protruding from the first opening portion 5a protrudes in a direction away from the distal end portion of the insertion portion 2 along the plane P.

Note that it is only necessary that the first opening portion 5a open at a position that the treatment instrument 20 protruding from the first opening portion 5a enters an observation range of the observation portion 4. For example, the first opening portion 5a may be provided on the bent portion 2c bent along the curve C1 of the insertion portion 2 or may be provided on the distal end portion 2a of the insertion portion 2. When the connection portion 2e in the straight line shape is provided between the bent portion 2c and the distal end portion 2a as in the first modification shown in FIG. 6, the first opening portion 5a may be provided on the connection portion 2e.

The treatment instrument insertion channel 5 is a conduit inserted into the bent portion 2c of the insertion portion 2 and connecting the first opening portion 5a and the second opening portion 5b. Note that the bending shape of the treatment instrument insertion channel 5 does not have to coincide with the bending shape of the bent portion 2c. For example, when the bending shape of the treatment instrument insertion channel 5 coincides with the bending shape of the bent portion 2c, there is an advantage that the electric cable 6 connected to the observation portion 4 can be installed in parallel with the treatment instrument insertion channel 5. In the present embodiment shown in FIG. 5, the treatment instrument insertion channel 5 is bent along the curve C1 on the plane P passing through the first opening portion 5a and the second opening portion 5b, just like the bent portion 2c.

Next, the arrangement of the shaft-shaped portion 3b of the grasping portion 3 will be described. The shaft-shaped portion 3b is installed to extend in the proximal end direction of the cystourethroscope 1 along the distal end cross section of the insertion portion 2, in other words, along the straight line L passing near the inflection portion of the insertion portion 2, on the plane P. In the first modification shown in FIG. 6, it is preferable that the straight line L coincide with or be parallel to the center axis of the linear connection portion 2e of the insertion portion 2. In the second modification shown in FIG. 7, it is preferable that the straight line L coincide with or be parallel to the center axis of the linear distal end portion 2a of the insertion portion 2.

Note that considering a size of a general subject, it is preferable that a length of a part partitioned by the curve C1 of the straight line L indicated by reference sign B of FIG. 5 be 180 to 215 mm. However, the present invention is not limited to the length, and the present invention can also be applied to a cystourethroscope with a longer insertion portion, for example. In that case, an example of the length of the part indicated by reference sign B is 260 to 295 mm. It is also preferable that among the part indicated by reference sign B, a length of a part (reference sign D) provided with the grasping portion 3 be 0 to 15 mm.

The observation portion 4 is installed on the distal end portion 2a of the insertion portion 2. The observation portion 4 of the present embodiment is, for example, an ultrasound observation portion including a plurality of ultrasound transducers and capable of transmitting and receiving ultrasound.

The observation portion 4 of the present embodiment has a form that is a so-called convex scanning system and is configured to be able to pick up an ultrasound tomographic image of the subject.

Specifically, the observation portion 4 includes a plurality of ultrasound transducers arranged in an arc shape and can drive the individual ultrasound transducers at predetermined timing to perform scanning in a substantially fan shape with an ultrasound beam along the plane P as shown in FIG. 4. Note that the ultrasound transducers can be, for example, piezoelectric devices or electrostrictive devices, such as piezoelectric ceramics, or ultrasound transducers based on micromachine technology (MUT; micromachined ultrasonic transducer).

The observation portion 4 is installed at a position that allows the treatment instrument 20 protruding from the first opening portion 5a to be housed within the observation range. More specifically, the observation portion 4 can perform scanning with the ultrasound beam toward the outside in the radial direction of the bent distal end portion 2a, and at least part of the treatment instrument 20 protruding from the first opening portion 5a enters a scanning range R (shown in FIG. 4).

The observation portion 4 can be electrically connected to an ultrasound observation apparatus that is an external apparatus not shown, through the electric cable 6 inserted into the insertion portion 2 and the cable 3c. The observation portion 4 is controlled by the ultrasound observation apparatus connected through the electric cable 6.

Note that the observation portion 4 may be able to pick up an optical image in the subject. When the observation portion 4 can pick up an optical image, the observation portion 4 includes, for example, an objective lens and an image pickup device, and an electric cable electrically connected to the image pickup device is installed in the insertion portion 2. Note that the observation portion 4 may be configured to transmit the optical image through an optical fiber installed in the insertion portion 2. When the observation portion can pick up an optical image, an illumination apparatus, such as an optical fiber for transmitting illuminating light and an LED, is installed in the insertion portion 2.

The observation portion 4 may include both of an ultrasound observation portion that can transmit and receive ultrasound and an optical observation portion that can pick up an optical image.

The cystourethroscope 1 may include, as the observation portion 4, an ultrasound observation portion that can transmit and receive ultrasound, and an endoscope that can pick up an optical image may be inserted into the treatment instrument insertion channel 5 to perform both of ultrasound observation and optical observation. Here, the endoscope that can pick up an optical image may be a rigid endoscope or may be a flexible endoscope.

The cystourethroscope 1 may include, as the observation portion 4, an optical observation portion that can pick up an optical image, and an ultrasound endoscope that can transmit and receive ultrasound may be inserted into the treatment instrument insertion channel 5 to perform both of ultrasound observation and optical observation. Here, the ultrasound endoscope that can transmit and receive ultrasound may be a rigid endoscope or may be a flexible endoscope.

Next, the treatment instrument 20 will be described. The treatment instrument 20 of the present embodiment includes: an insertion portion 21 as a part that can be inserted into the treatment instrument insertion channel 5 of the cystourethroscope 1 described above; and an operation portion 22 provided at a proximal end of the insertion portion 21. The treatment instrument 20 of the present embodiment is a biopsy needle in which a distal end portion of the insertion portion 21 can be punctured to the prostate to collect tissue of the prostate. A basic structure of the biopsy needle is publicly known, and therefore details will not be described.

Figure 9:
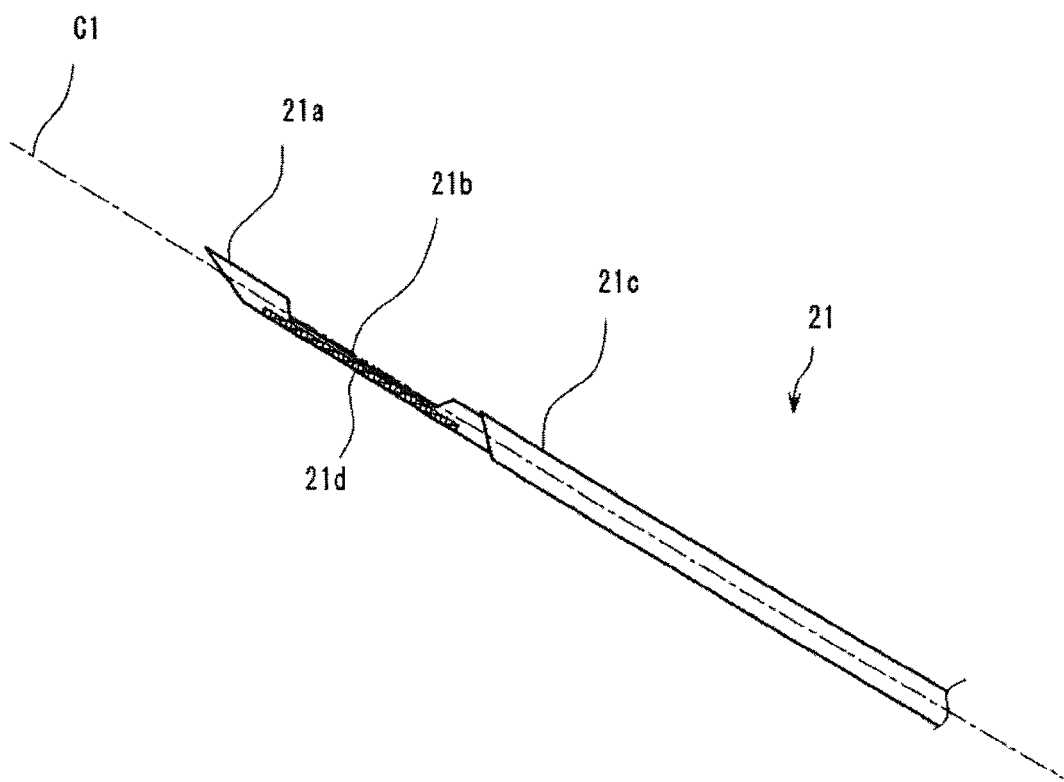
FIG. 9 is a diagram enlarging a distal end portion of an insertion portion of the treatment instrument.

Schematically, as shown in FIG. 9, the insertion portion 21 includes: an inner needle 21a in a needle shape; a notch 21b in a concave shape provided on a distal end portion of the inner needle 21a; and an outer needle 21c that is a tubular member covering the surrounding of the inner needle 21a and that can be moved relative to the inner needle 21a. The inner needle 21a and the outer needle 21c can be moved by operation of a knob in the operation portion 22.

To collect the tissue of the prostate by the treatment instrument 20, both of the inner needle 21a and the outer needle 21c are first punctured to near a site to be sampled. Next, only the inner needle 21a is punctured to the biopsy site up to the part of the notch 21b, and then the outer needle 21c is moved in the distal end direction toward the inner needle 21a. As a result of the operation, the tissue of the desired site in the prostate can be introduced to a space of the notch 21b in the outer needle 21c.

Figure 8:
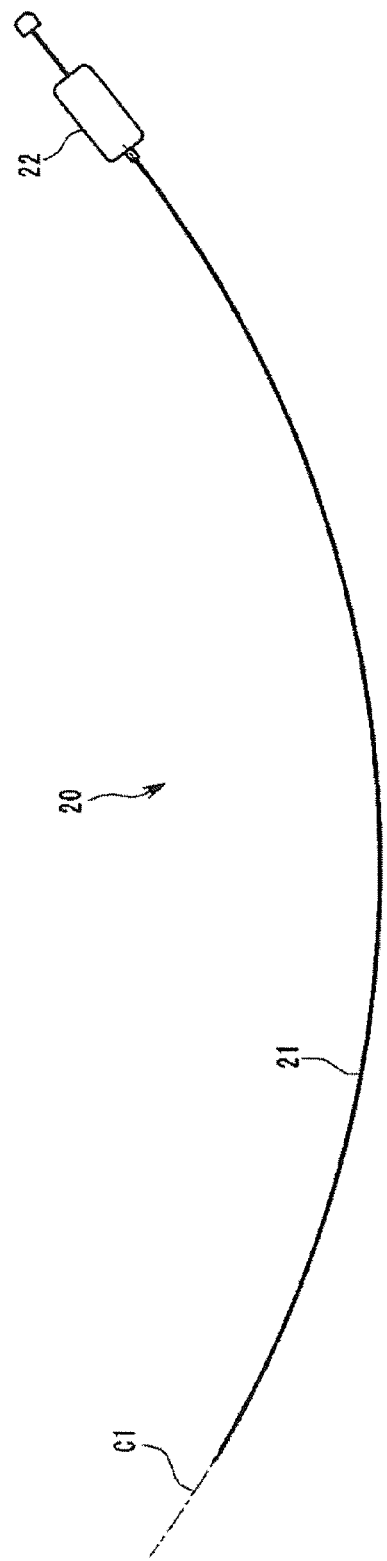
FIG. 8 is a side view of a treatment instrument.

As shown in FIG. 8, the treatment instrument 20 of the present embodiment is formed such that the insertion portion 21 as a part that can be inserted into the treatment instrument insertion channel 5 maintains a bent shape just like the curve C1, in the state under no external force. That is, the insertion portion 21 of the treatment instrument 20 of the present embodiment has a substantially arc shape that is bent with substantially the same radius of curvature as that of the treatment instrument insertion channel 5 of the cystourethroscope 1. Note that the radius of curvature of the insertion portion 21 does not have to completely coincide with the radius of curvature of the curve C1, and it is only necessary that the radius of curvature of the insertion portion 21 be a value substantially close to the radius of curvature of the curve C1.

In this way, the insertion portion 21 has a bent shape, and therefore the insertion portion 21 of the treatment instrument 20 can be easily and quickly inserted into the treatment instrument insertion channel 5 of the cystourethroscope 1 with small force.

In the present embodiment, to clearly indicate the insertion portion 21 on the ultrasound tomographic image, the insertion portion 21 is provided with an ultrasound scattering portion 21d as shown in FIG. 9, in which a surface is coarse so that irradiated ultrasound is scattered. The ultrasound scattering portion 21d is provided only on an outer circumferential portion outside in a radial direction of the insertion portion 21 bent in a substantially arc shape. This is because since the insertion portion 21 is bent according to the bending of the treatment instrument insertion channel 5, the outer circumferential portion outside in the radial direction of the insertion portion 21 always faces the observation portion 4 when the insertion portion 21 protrudes from the first opening portion 5a. In this way, a range provided with the ultrasound scattering portion 21d is narrow, and therefore a cost necessary for production can be reduced. Note that although the ultrasound scattering portion 21d is provided only on the inner needle 21a in the present embodiment shown in FIG. 9, the ultrasound scattering portion 21d may be provided only on the outer needle 21b or may be provided on both of the inner needle 21a and the outer needle 21b.

Figure 10:
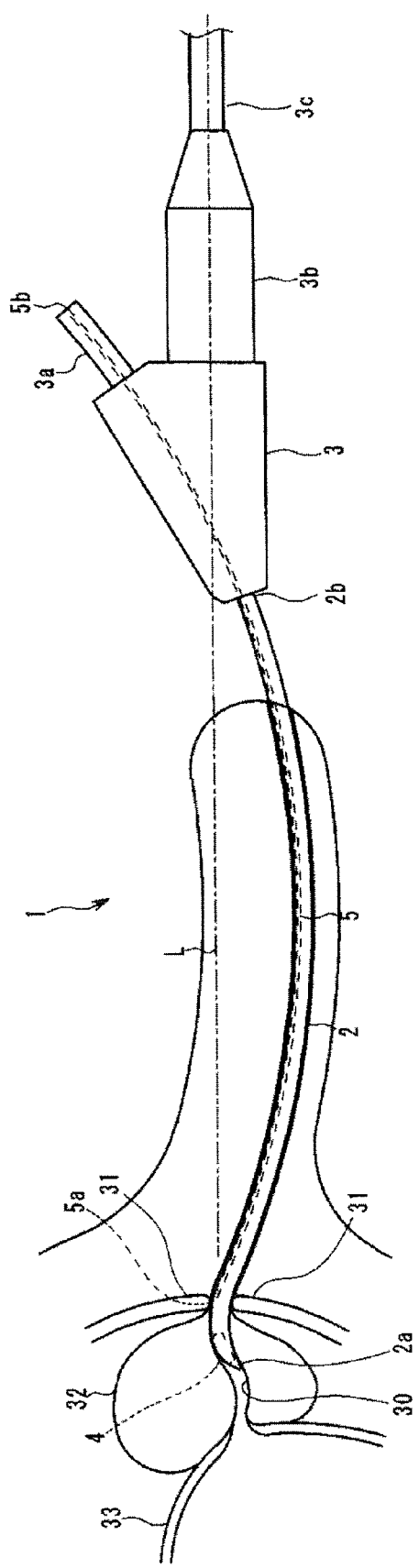
FIG. 10 is a schematic diagram showing a state in which the distal end portion of the insertion portion is inserted up to a part where a prostate exists.

Effects of the cystourethroscope 1 and the treatment instrument 20 of the present embodiment described above will be described. FIG. 10 is a schematic diagram showing a state in which the cystourethroscope 1 is inserted into a urethra 30 of a human body until the distal end portion 2a of the insertion portion 2 and the first opening portion 5a reach a site where a prostate 32 exists.

As shown in FIG. 10, when the cystourethroscope 1 of the present embodiment is used, the distal end portion 2a of the insertion portion 2 and the first opening portion 5a are positioned on a back side (bladder side) of a urethral sphincter 31. In an actual procedure, whether the cystourethroscope 1 is inserted up to the position indicated in FIG. 10 is checked by using an ultrasound tomographic image or an optical image picked up by the observation portion 4 or using an optical image obtained by the endoscope inserted into the treatment instrument insertion port.

Figure 11:
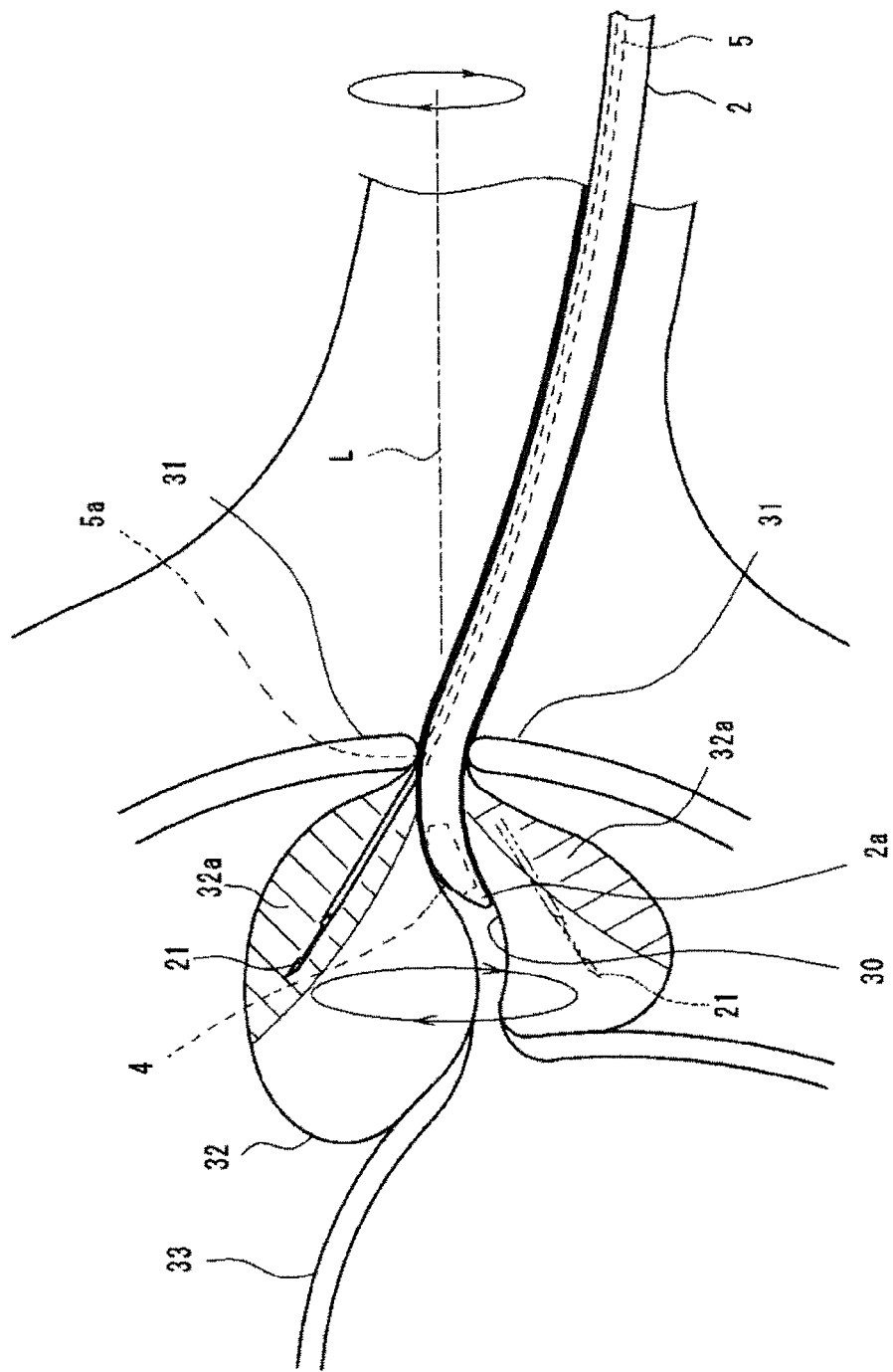
FIG. 11 is a partial enlarged view of FIG. 8.

Here, the treatment instrument insertion channel 5 communicated with the first opening portion 5a and the distal end portion 2a that is a part on the distal end side of the first opening portion 5a of the insertion portion 2 are bent in opposite directions. Therefore, as shown in FIG. 11, the insertion portion 21 of the treatment instrument 20 protruding from the first opening portion 5a protrudes in a direction away from the urethra 30. Note that the protrusion operation of the treatment instrument 20 is performed while the ultrasound tomographic image picked up by the observation portion 4 is checked.

As described, if the insertion portion 2 is inserted into the urethra such that the first opening portion 5a is positioned in the region where the prostate 32 exists, the treatment instrument 20 inserted into the treatment instrument insertion channel 5 protrudes at an angle relative to the urethra in the present embodiment. Therefore, according to the cystourethroscope 1 and the treatment instrument 20 of the present embodiment, the insertion portion 21 of the treatment instrument 20 can be easily punctured to a peripheral area 32a of the prostate 32 without being restricted much by the urethral sphincter 31. The peripheral area 32a of the prostate 32 is generally a site where cancer frequency occurs. That is, according to the present embodiment, the prostate biopsy through the urethra can be easily performed.

Furthermore, the fact that the operation of the cystourethroscope 1 and the treatment instrument 20 are not easily restricted by the urethral sphincter 31 means that stimulation of the urethral sphincter 31 is reduced. That is, suffering of a patient in the procedure, such as a pain and an unnatural feeling, is reduced. Therefore, anesthesia in the prostate biopsy can be light in the present embodiment, and the prostate biopsy can be finished quickly.

Figure 12:
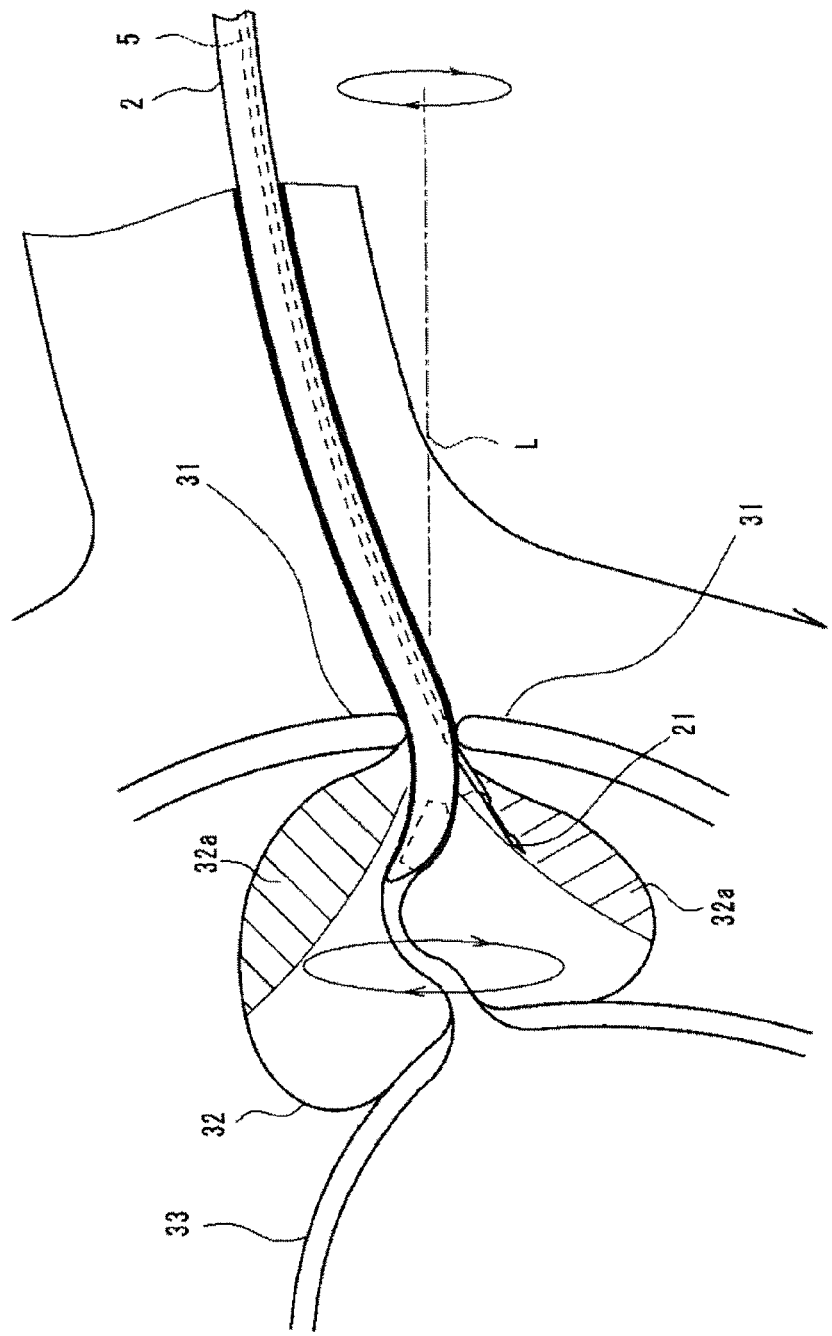
FIG. 12 is a schematic diagram showing a state in which a shaft-shaped portion is rotated 180 degrees from the state of FIG. 8.

In the present embodiment, the shaft-shaped portion 3b of the grasping portion 3 extends along the straight line L passing near the first opening portion 5a as shown in FIG. 10. Therefore, when the user grasps the shaft-shaped portion 3b to rotate the cystourethroscope 1 around the substantially center axis of the shaft-shaped portion 3b in the state that the insertion portion 2 is inserted into the urethra 30 as shown in FIG. 10, the insertion portion 2 rotates around the straight line L without significantly stimulating the urethral sphincter 31. FIG. 12 shows a state in which the shaft-shaped portion 3b is rotated 180 degrees from the state of FIG. 11. In this case, the protrusion direction of the treatment instrument 20 protruding from the first opening portion 5a also rotates around the straight line L. Therefore, the treatment instrument 20 can be punctured to a region along a conical surface, with the straight line L serving as a substantially center axis.

As described, the cystourethroscope 1 and the treatment instrument 20 of the present embodiment can be used to easily and quickly carry out the prostate biopsy without much suffering, even if the tissue is collected from a plurality of parts. Accuracy of diagnosis can be improved by increasing the parts from which the tissue is collected, and this is preferable.

Furthermore, the urethral sphincter 31 is not much stimulated when the part of the tissue to be collected is changed. Therefore, the anesthesia in the prostate biopsy can be light, and the prostate biopsy can be finished quickly.

Note that although the insertion portion 21 of the treatment instrument 20 has a bent shape just like the bending shape of the treatment instrument insertion channel 5 in the embodiment described above, the insertion portion 21 of the treatment instrument 20 may have a substantially straight line shape like a conventionally used biopsy needle as long as the insertion portion 21 can be elastically deformed according to the bending shape of the treatment instrument insertion channel 5. In this case, although the force necessary to insert the insertion portion 21 of the treatment instrument 20 into the treatment instrument insertion channel 5 increases, the other effects are the same as those in the embodiment described above.

Figure 13:
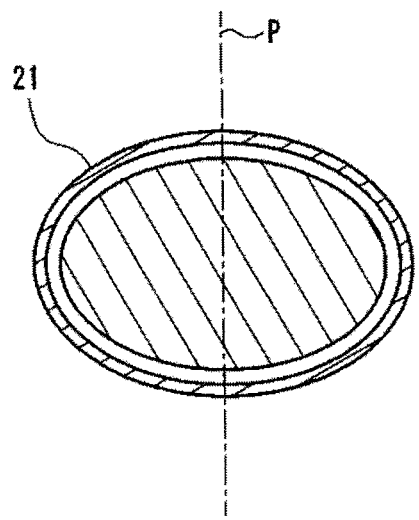
FIG. 13 is a cross-sectional view for describing a first modification of the treatment instrument.

Next, a first modification of the insertion portion 21 of the treatment instrument 20 will be described. FIG. 13 illustrates a cross-sectional shape of the insertion portion 21. As in the first modification shown in FIG. 13, the insertion portion 21 may have a flat shape, such as a substantially elliptic shape and a substantially oval shape, in which a major axis is a direction substantially orthogonal to the plane P including the curve C1 along which the insertion portion 21 runs. In other words, an area of an outer circumferential surface facing outside in the radial direction of the bent insertion portion 21 increases in the first modification. Therefore, the insertion portion 21 is more clearly depicted in the ultrasound tomographic image picked up by the observation portion 4. Furthermore, deformation in the direction along the plane P is facilitated, and the force necessary to elastically deform the insertion portion 21 of the treatment instrument 20 into a substantially straight line shape is smaller than that when the cross-sectional shape is circular. Therefore, the force necessary to insert the insertion portion 21 into the treatment instrument insertion channel 5 can be reduced.

Figure 14:
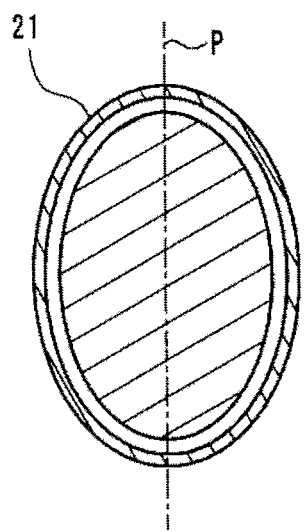
FIG. 14 is a cross-sectional view for describing a second modification of the treatment instrument.

Next, a second modification of the insertion portion 21 of the treatment instrument 20 will be described. FIG. 14 illustrates a cross-sectional shape of the insertion portion 21. As in the second modification shown in FIG. 14, the insertion portion 21 may have a flat shape, such as a substantially elliptic shape and a substantially oval shape, in which a major axis is a direction substantially parallel to the plane P including the curve C1 along which the insertion portion 21 runs. In the second modification, strength for keeping the bending shape of the insertion portion 21 can be improved.

Figure 15:
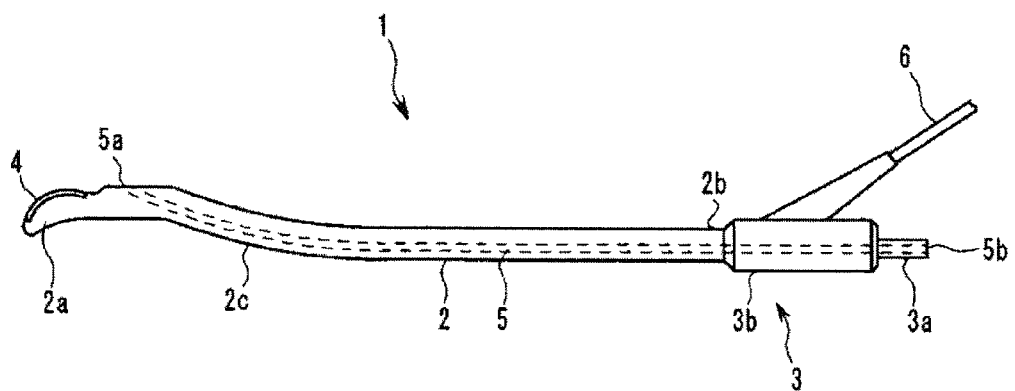
FIG. 15 is a diagram showing a third modification of the cystourethroscope for prostate biopsy.

Note that although the insertion portion 2 has a bent shape even near the proximal end portion 2b in the present embodiment described above, the insertion portion 2 may have a straight line shape near the proximal end portion 2b of the insertion portion 2 as shown for example in FIG. 15.

Figure 16:
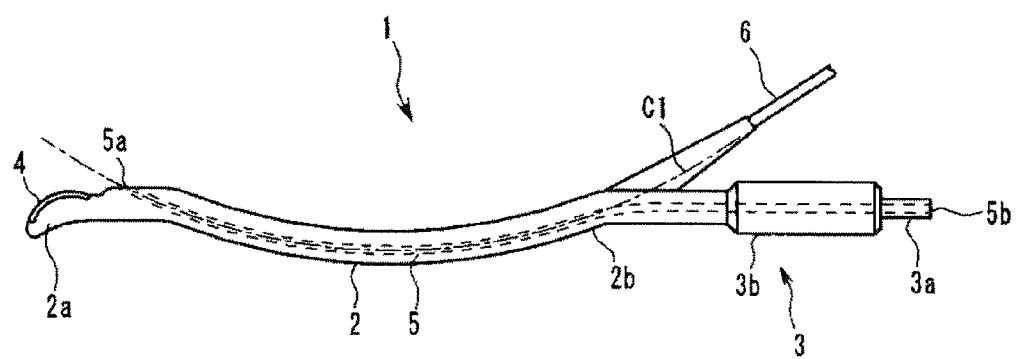
FIG. 16 is a diagram showing a fourth modification of the cystourethroscope for prostate biopsy.

Although the treatment instrument insertion channel 5 is installed to be bent along the curve C1 in the present embodiment described above, the treatment instrument insertion channel 5 may be installed out of the curve C1, along the center axis of the shaft-shaped portion 3b in the grasping portion 3, as shown for example in FIG. 16.

Second Embodiment

Hereinafter, a second embodiment of the present invention will be described. Only differences from the first embodiment will be described below. The same constituent elements as those in the first embodiment are designated with the same reference signs, and the description will be appropriately skipped.

Figure 17:
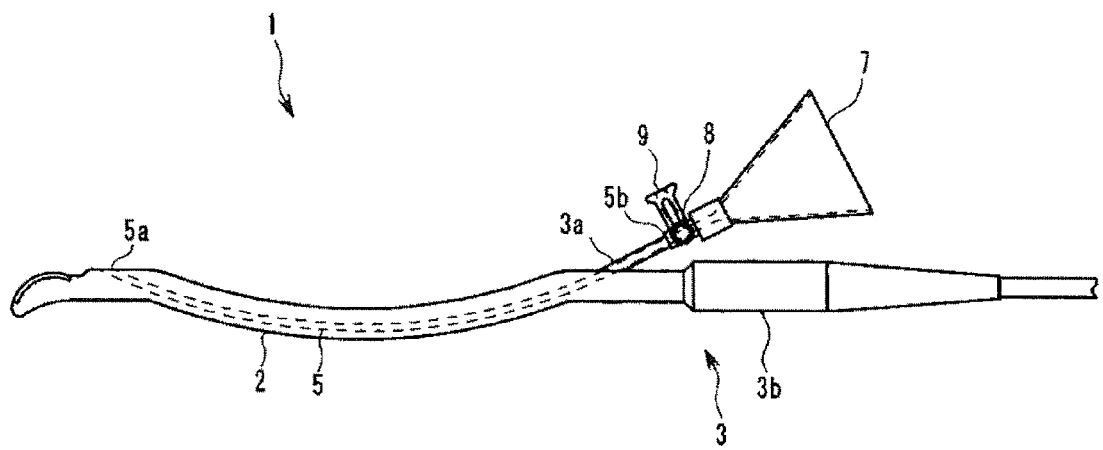
FIG. 17 is a side view of the cystourethroscope for prostate biopsy of a second embodiment.

As shown in FIG. 17, the cystourethroscope 1 of the present embodiment is different from the first embodiment in that a treatment instrument insertion port 7, a perfusion water filling port 9, and a cock 8 are installed on the treatment instrument insertion pipe sleeve 3a.

The treatment instrument insertion port 7 is a funnel-shaped member with a diameter reduced toward the second opening portion 5b. In other words, the treatment instrument insertion port 7 is a member with a shape that widens the second opening portion 5b toward the proximal end side. The treatment instrument insertion port 7 can be attached to and detached from the treatment instrument insertion pipe sleeve 3a through, for example, a screw mechanism called a Luer lock.

The perfusion water filling port 9 is an opening portion for pouring a perfusate into the treatment instrument insertion channel 5 and is communicated with the treatment instrument insertion channel 5. The perfusion water filling port 9 can be opened and closed by the cock 8.

The insertion portion 21 of the treatment instrument 20 can be easily introduced into the treatment instrument insertion channel 5 by providing the funnel-shaped treatment instrument insertion port 7 on the treatment instrument insertion pipe sleeve 3a as in the present embodiment.

Figure 18:
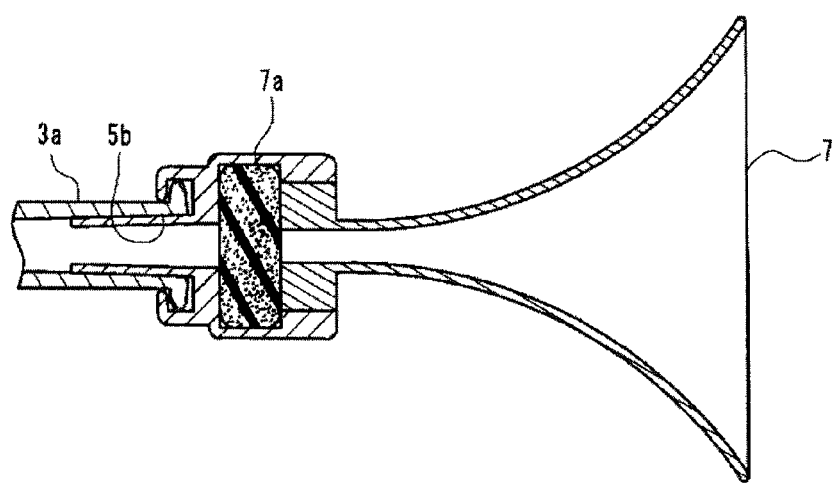
FIG. 18 is a cross-sectional view of a treatment instrument insertion port.

Note that as shown in a cross-sectional view of the treatment instrument insertion port 7 of FIG. 18, a sponge rubber 7a may be installed in the treatment instrument insertion port 7 so as to close the second opening portion 5b. The distal end of the insertion portion 21 of the treatment instrument 20 can penetrate through the sponge rubber 7a.

Figure 19:
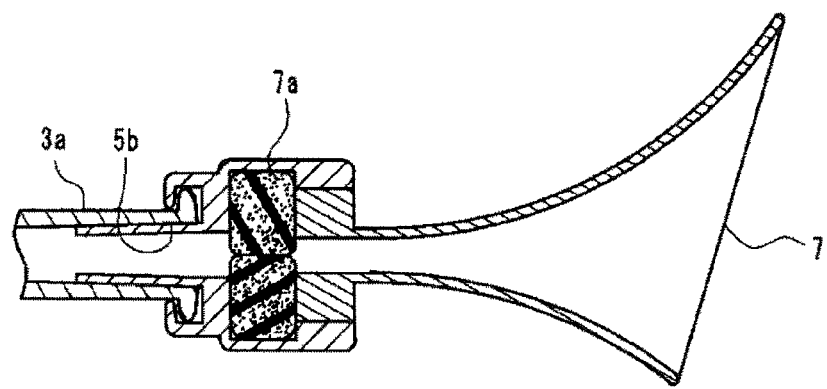
FIG. 19 is a diagram showing a first modification of the treatment instrument insertion port.

The installation of the sponge rubber 7a in the treatment instrument insertion port 7 as in FIG. 18 can prevent the perfusate from flowing out from the treatment instrument insertion port 7. Note that the sponge rubber 7a may be divided into two parts at a center portion as shown in FIG. 19 so that the insertion portion 21 of the treatment instrument 20 can easily penetrate. An example of a method of allowing the insertion portion 21 to easily penetrate through the sponge rubber 7a includes formation of a cut or a through hole on the sponge rubber 7a.

Note that the shape of the treatment instrument insertion port 7 may be conical, or the shape of the treatment instrument insertion port 7 may be a pyramid shape, such as a triangular pyramid and a quadrangular pyramid. The shape is not limited to a shape in which the diameter is linearly enlarged in the opening direction as shown in FIG. 17. The shape may be a shape in which inclinations of inner wall surfaces relative to the center axis increase in the opening direction (shape in which the inner wall surfaces are convex inward) as shown in FIG. 18. Conversely, the shape may be a bell shape in which the inclinations of the inner wall surfaces relative to the center axis decrease in the opening direction (shape in which the inner wall surfaces are convex outward).

Figure 20:
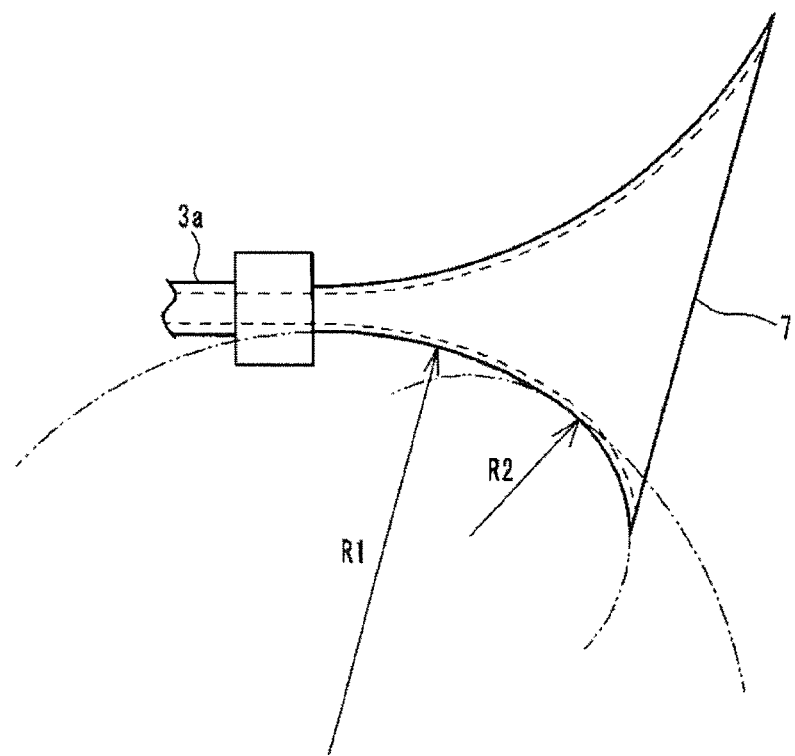
FIG. 20 is a diagram showing a second modification of the treatment instrument insertion port.
Figure 21:
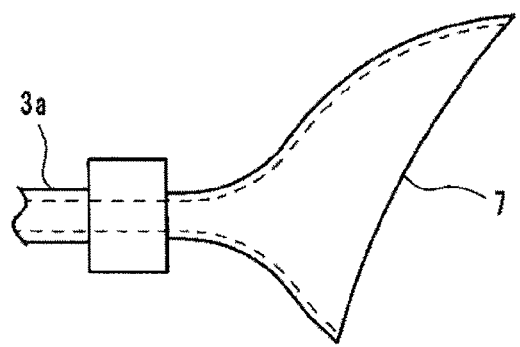
FIG. 21 is a diagram showing a third modification of the treatment instrument insertion port.

When a cross-sectional shape of the treatment instrument insertion port 7 in an axial direction is a shape along the curve, the radius of curvature may change in the middle as shown in FIG. 20. In an example shown in FIG. 20, a radius of curvature R1 of the wall surface of the treatment instrument insertion port 7 at a part close to the treatment instrument insertion pipe sleeve 3a is greater than a radius of curvature R2 of a part close to the opening end of the treatment instrument insertion port 7. The cross-sectional shape of the treatment instrument insertion port 7 in the axial direction may also be a shape in which directions of concavity and convexity of the inner wall surfaces are inverted in the middle as shown in FIG. 21.

The opening end of the treatment instrument insertion port 7 may have a shape cut out by a plane substantially orthogonal to the center axis of the treatment instrument insertion pipe sleeve 3a as shown in FIG. 18 or may have a shape cut out by a plane at a predetermined angle relative to the center axis of the treatment instrument insertion pipe sleeve 3a as shown in FIG. 19. The opening end of the treatment instrument insertion port 7 may have a shape cut out by a curved surface as shown in FIG. 21.

Third Embodiment

Hereinafter, a third embodiment of the present invention will be described. Only differences from the second embodiment will be describe below. The same constituent elements as those in the second embodiment are designated with the same reference signs, and the description will be appropriately skipped.

Figure 22:
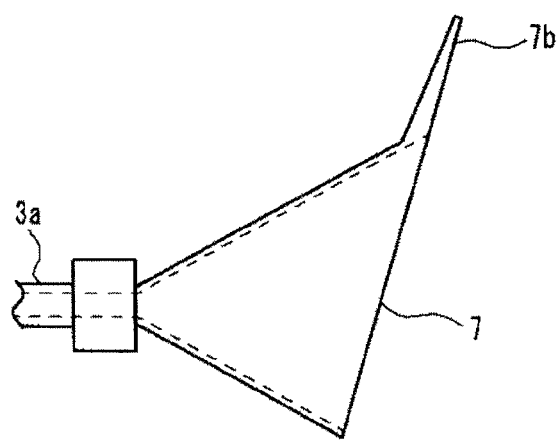
FIG. 22 is a side view of the treatment instrument insertion port of a third embodiment.
Figure 23:
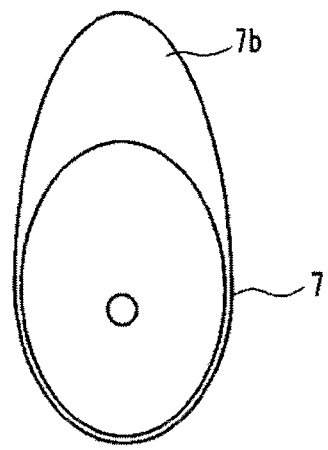
FIG. 23 is a diagram of the treatment instrument insertion port of the third embodiment as viewed from an opening direction.

As shown in FIGS. 22 and 23, the treatment instrument insertion port 7 of the present embodiment is different from the second embodiment in that the treatment instrument insertion port 7 includes a plate-shaped tongue piece portion 7b extending toward the outside from an outer edge portion of the opening end. Note that although a plane shape of the tongue piece portion 7b of the present embodiment is an elliptic shape as shown in FIG. 23, the plane shape of the tongue piece portion 7b is not limited to this, and the plane shape may be rectangular, trapezoidal, or the like.

In this way, the tongue piece portion 7b extending toward the outside from the opening end is provided on the treatment instrument insertion port 7. This can prevent the distal end of the treatment instrument 20 from coming in contact with a hand of the user, the grasping portion 3, and the like even if the distal end of the treatment instrument 20 comes out from the opening of the treatment instrument insertion port 7 when the treatment instrument 20 is inserted into the treatment instrument insertion port 7.

Figure 24:
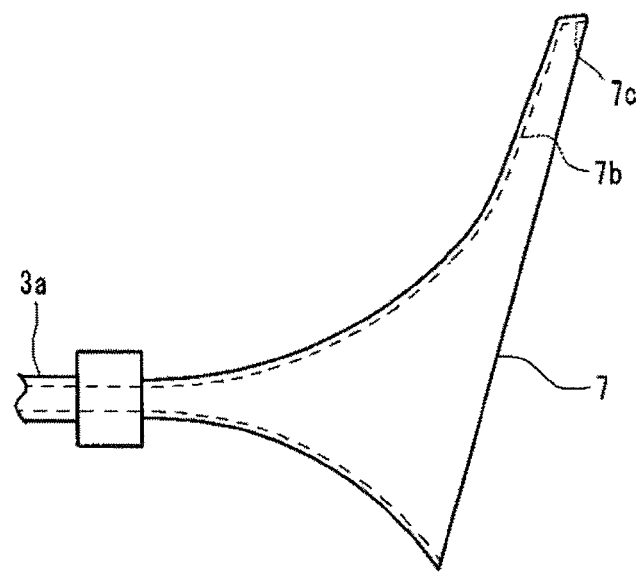
FIG. 24 is a diagram showing a first modification of the treatment instrument insertion port of the third embodiment.

Furthermore, the distal end of the treatment instrument 20 colliding with the tongue piece portion 7b can be surely guided into the opening if the tongue piece portion 7b is provided with a wall portion 7c enclosing the surrounding and protruding in the opening direction as shown in FIG. 24.

Figure 25:
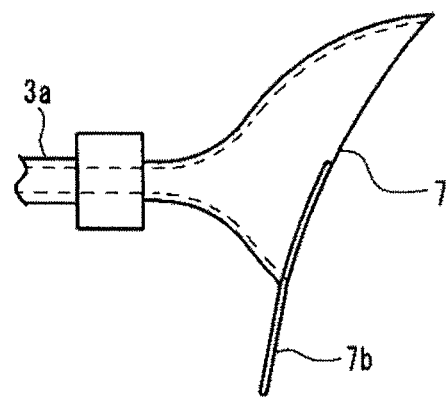
FIG. 25 is a diagram showing a second modification of the treatment instrument insertion port of the third embodiment.
Figure 26:
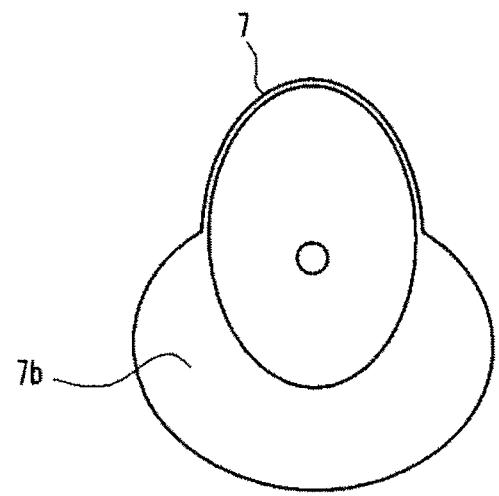
FIG. 26 is a diagram showing the second modification of the treatment instrument insertion port of the third embodiment.

Note that tongue piece portion 7b is not limited to the shape extending in one direction from the outer edge portion of the opening end, and the shape may be a shape extending toward the outside from the entire surrounding or a predetermined range of the opening of the treatment instrument insertion port 7. The tongue piece portion 7b of a modification shown in FIGS. 25 and 26 has a shape extending toward the outside from a range at about a half of the surrounding of the opening of the treatment instrument insertion port 7.

Note that the present invention is not limited to the first to third embodiments, and the present invention can be appropriately changed within the scope and the spirit of the inventions that can be read from the claims and the entire specification. The changed rigid endoscopes and treatment instruments are also included in the technical scope of the present invention.

What is claimed is:

1. An endoscope for prostate biopsy comprising:

a rigid insertion portion that includes an ultrasound transmission and reception portion that transmits and receives ultrasound, a distal end portion including the ultrasound transmission and reception portion, and a bent portion which is provided on a proximal end side of the distal end portion and which is bent at a predetermined curvature, the insertion portion being configured to be unyielding to natural or surgically created body cavities or instrument channels;

a treatment instrument insertion channel that passes through inside the bent portion and includes a first opening portion provided on a distal end side and a second opening portion provided on a proximal end side, the treatment instrument insertion channel being installed at a position that allows a treatment instrument protruding from the first opening portion to be housed within an observation range of the ultrasound transmission and reception portion;

a shaft-shaped portion that is installed to extend in a proximal end direction of the bent portion along a straight line passing through an inflection portion provided between the distal end portion and the bent portion, the shaft-shaped portion being configured to be grasped by an operator; and a grasping portion that includes the shaft-shaped portion.

2. The endoscope for prostate biopsy according to claim 1, wherein the curvature of the bent portion is constant.

3. A treatment instrument that is at least partially insertable into the treatment instrument insertion channel of the endoscope for prostate biopsy according to claim 1, wherein a part that can be inserted into the treatment instrument insertion channel maintains a shape bent along the treatment instrument insertion channel in a state under no external force.

4. An endoscope for prostate biopsy comprising:

a rigid insertion portion that includes an ultrasound transmission and reception portion that transmits and receives ultrasound, a distal end portion including the ultrasound transmission and reception portion, and a bent portion which is provided on a proximal end side of the distal end portion and which is bent at a predetermined curvature, the insertion portion being configured to be unyielding to natural or surgically created body cavities or instrument channels;

a treatment instrument insertion channel that passes through inside the bent portion and includes a first opening portion provided on a distal end side and a second opening portion provided on a proximal end side, the treatment instrument insertion channel being installed at a position that allows a treatment instrument protruding from the first opening portion to be housed within an observation range of the ultrasound transmission and reception portion; and a shaft-shaped portion that is installed to extend in a proximal end direction of the bent portion along a straight line coincident with or parallel to a center axis of a connection portion provided between the distal end portion and the bent portion, the shaft-shaped portion being configured to be grasped by an operator; and a grasping portion that includes the shaft-shaped portion.

5. An endoscope for prostate biopsy comprising:

a rigid insertion portion that includes an ultrasound transmission and reception portion that transmits and receives ultrasound, a linear distal end portion including the ultrasound transmission and reception portion, and a bent portion which is provided on a proximal end side of the distal end portion and which is bent at a predetermined curvature, the insertion portion being configured to be unyielding to natural or surgically created body cavities or instrument channels;

a treatment instrument insertion channel that passes through inside the bent portion and includes a first opening portion provided on a distal end side and a second opening portion provided on a proximal end side, the treatment instrument insertion channel being installed at a position that allows a treatment instrument protruding from the first opening portion to be housed within an observation range of the ultrasound transmission and reception portion;

a shaft-shaped portion that is installed to extend in a proximal end direction of the bent portion along a straight line coincident with or parallel to a center axis of the linear distal end portion, the shaft-shaped portion being configured to be grasped by an operator; and a grasping portion that includes the shaft-shaped portion.

* * * * *